United States Patent [19]

List et al.

[11] 4,067,779
[45] Jan. 10, 1978

[54] PROCESS FOR THE PURIFICATION OF 1,10-DECANEDICARBOXYLIC ACID

[75] Inventors: Ferdinand List, Marl; Otto Rauhut, Hamm uber Marl; Peter Hegenberg; Rudolf Strobele, both of Marl, all of Germany

[73] Assignee: Chemische werke Huis Aktiengesellschaft, Marl, Germany

[21] Appl. No.: 572,857

[22] Filed: Apr. 29, 1975

[30] Foreign Application Priority Data

Apr. 29, 1974  Germany .............................. 2420765

[51] Int. Cl.² .......................... B01D 3/10; C07C 55/02
[52] U.S. Cl. ........................................ 203/28; 203/31; 203/89; 203/91; 260/537 P
[58] Field of Search .................. 203/31, 28, 42, 39, 203/89, 91-94, 14, 6; 260/537 P

[56] References Cited

U.S. PATENT DOCUMENTS

| | | | |
|---|---|---|---|
| 2,522,529 | 9/1950 | Miller et al. | 203/89 |
| 2,771,482 | 11/1956 | Brown, Jr. et al. | 260/537 |
| 2,791,551 | 5/1957 | Ash et al. | 203/89 |
| 2,791,598 | 5/1957 | Brown, Jr. et al. | 260/537 |
| 2,878,276 | 3/1959 | Crowley et al. | 260/537 |
| 3,290,369 | 12/1966 | Bonfield et al. | 260/537 P |
| 3,402,108 | 9/1968 | Oehlschlaeger et al. | 203/31 |
| 3,637,832 | 1/1972 | White et al. | 260/537 P |
| 3,761,517 | 9/1973 | Rohl et al. | 260/537 P |
| 3,880,921 | 4/1975 | Hellemanns et al. | 260/537 P |
| 3,903,152 | 9/1975 | Matsubara et al. | 260/537 P |
| 3,979,450 | 9/1976 | Moskovich et al. | 260/537 |

*Primary Examiner*—Wilbur L. Bascomb, Jr.
*Attorney, Agent, or Firm*—Millen & White

[57] ABSTRACT

Crude 1,10-decanedicarboxylic acid produced by the nitric acid oxidation at 20°—60° C. of cyclododecanone, cyclododecanol or a mixture thereof can be purified by distillation to a purity suitable for use in the production of polyamides and polyesters by reducing prior to distillation, e.g., by heating to 70°-90° C., the organically bound nitrogen content and as required the nitric acid content, e.g., by washing, and water content thereof so that the sample which is distilled has maximum contents thereof of 0.05%, 0.02% and 0.1% by weight, respectively, and distilling the pre-purified sample at a sump temperature of 215°-225° C. and at a pressure of 0.5 – 2 torr.

12 Claims, 1 Drawing Figure

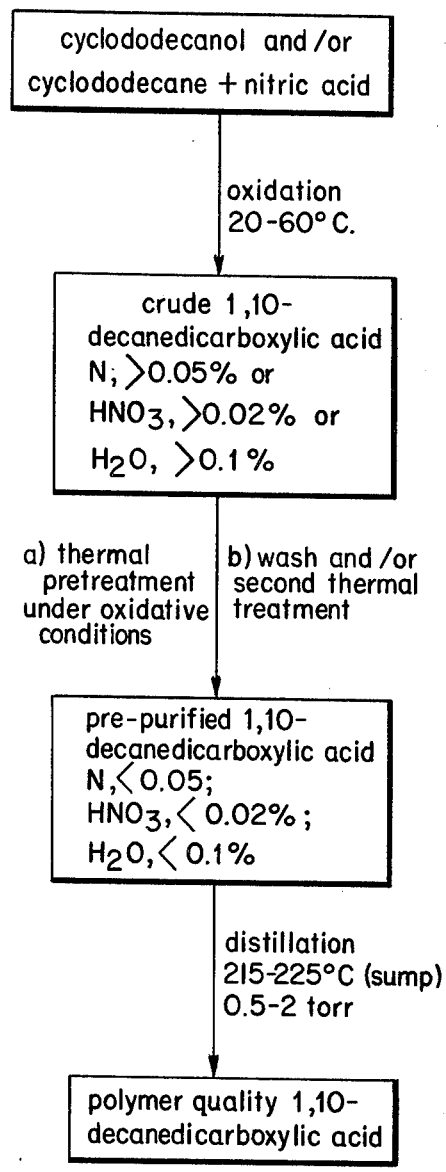

PROCESS FOR THE PURIFICATION OF 1,10-DECANEDICARBOXYLIC ACID

BACKGROUND OF THE INVENTION

This invention relates to a process for the purification of 1,10-decanedicarboxylic acid.

1,10-Decanedicarboxylic acid (DDA) is a valuable starting compound for the production of polymers, such as polyamides and polyesters. A number of methods for the production of 1,10-decanedicarboxylic acid are known from the literature. Ordinarily, cyclododecanone or cyclododecanol or a mixture thereof is oxidized to 1,10-decanedicarboxylic acid by oxidation with nitric acid under mild conditions, usually in the presence of oxidation catalysts such as, for example, copper salts and vanadium salts.

Heretofore, great difficulties have been encountered in obtaining, in a simple manner, 1,10-decanedicarboxylic acid in the purity required, for example, when used as a polyamide or polyester component. It also has been especially difficult to produce 1,10-decanedicarboxylic acid with very low color numbers, i.e., in the so-called fiber quality.

According to German Pat. No. 737,691, it is practically impossible to purify longer-chain $\alpha,\omega$-dicarboxylic acids by distillation. It is indicated in French Pat. No. 1,393,569 that nitrogen-containing compounds are formed during the oxidation of cycloalkanols and cycloalkanones with nitric acid to obtain $\alpha,\omega$-dicarboxylic acids, and that these byproducts impair the thermal stability of the product. The aforementioned patent discloses that the dicarboxylic acids are obtained in a sufficiently pure form by recrystallization from organic solvents.

A number of literature references are known wherein the attempt is made to obtain very pure 1,10-decanedicarboxylic acid by recrystallization, melt crystallization, or similar methods. (See, for example, French Pat. No. 1,393,568; U.S. Pat. No.3,413,138; German Unexamined Laid-Open Application DOS No. 1,443,811; German Pat. No. 1,903,571; and DOS No. 2,101,942.) Thus, heretofore, it was necessary to employ complicated and expensive recrystallization processes to obtain 1,10-decanedicarboxylic acid of high purity.

It is an object of this invention to provide a method of purifying, by a simple method, 1,10-decanedicarboxylic acid produced by the nitric acid oxidation of cyclododecanol and/or cyclododecanone with nitric acid to such an extent that it can be used directly as a polyester or polyamide component.

SUMMARY OF THE INVENTION

According to this invention, crude 1,10-decanedicarboxylic acid obtained by the nitric acid oxidation under low temperature mild conditions of cyclododecanol and/or cyclododecane with nitric acid is purified to high quality by distillation by thermally pretreating the crude acid prior to distillation to an organically bound nitrogen content of 0.05% by weight or less, and, if required, reducing the free nitric acid content to 0.02% by weight or less and optionally to a water content of 0.1% by weight or less; and then distilling the pretreated 1,10-decanedicarboxylic acid at a sump temperature of 215°-225° C. and a pressure of 0.50- 2 torr.

DETAILED DISCUSSION

The starting 1,10-decanedicarboxylic acid for the purification process of this invention is obtained by the wellknown oxidation of cyclododecanol, cyclododecanone, or a mixture thereof with nitric acid under mild conditions, optionally in the presence of an oxidation catalyst. See U.S. Pat. No. 3,761,517; French Pat. No. 1,428,374, German Laid-Open Application DOS No. 2 217 003, which corresponds to Hellemanns et al. Ser. No. 348,124 filed Apr. 5, 1973, now U.S. 3,880,921. They are characterized in unrecrystallized form, by the presence therein of at least one of organically bound nitrogen, nitric acid and water, in an amount substantially in excess of 0.05%, 0.02% and 0.1% by weight respectively, e.g., about 0.1%, 0.05% and 0.2% or higher, respectively. Typically, depending on the oxidation method employed, 1,10-decanedicarboxylic acid as conventionally isolated from the nitric acid oxidation mixture will contain 0.2% organic nitrogen; 0.1% nitric acid; and 0.5% water.

This invention is based upon the discovery that if such starting 1,10-decanedicarboxylic acid is purified by distillation and, prior to distillation it is subjected to a pre-purification so that the organic nitrogen, nitric acid and water contents thereof are no more than 0.05%, 0.02% and 0.1% by weight, respectively, and the distillation is conducted at a sump temperature of 215°-225° C. and at a pressure of 0.5 - 2 torr., 1,10-decanedicarboxylic acid of a purity suitable for use directly in the production of polyamides and polyesters is obtained.

Prior to the distillation step of the process of this invention, the 1,10-decanedicarboxylic acid must have an organically bound nitrogen content of 0.05% by weight or less, preferably 0.02% by weight or less.

If the proportion of organically bound nitrogen in the 1,10-decanedicarboxylic acid which is distilled is more than a maximum of 0.05% by weight, the distillation yields only products having unsatisfactory color values. Also, undesirably high amounts of distillation residues are formed during the distillation. The organically bound nitrogen content is determined by the kjeldahl analysis.

With decanedicarboxylic acid produced under mild oxidation conditions, the term "mild conditions" meaning primarily low oxidation temperatures, e.g., 20°-60° C., preferably 30°-50° C., the reduction of organically bound nitrogen to 0.05% by weight or less can be accomplished by treatment of the crude 1,10-decanedicarboxylic acid under oxidative conditions. For this purpose, the crude acid could be treated with a strong oxidizing agent, such as permanganate, e.g., potassium permanganate, chromate, e.g., potassium dichromate, or hypochlorite, e.g., sodium hypochlorite, generally in an aqueous alkaline medium.

It is of special advantage to lower the organically bound nitrogen content by subjecting the crude product from the nitric acid oxidation stage, which still contains the oxidizing agent, consisting substantially of residual nitric acid, directly to a thermal treatment. Normally, a temperature of 70°-90° C. is sufficient.

If a starting 1,10-decanedicarboxylic acid is employed which was produced according to the processes of German Laid-Open Applications DOS Nos. 1,919,228; DOS 2,001,182; and DOS 2,217,003 (U.S. Pat. No. 3,761,517 and Application Ser. No. 348,124 filed Apr. 5, 1973), the organically bound nitrogen content may already be so low that it is merely necessary to lower the nitric acid and water contents thereof.

The free nitric acid content of the starting 1,10-decanedicarboxylic acid must be 0.02% by weight or less, preferably 0.01% by weight or less, prior to distillation. The following table shows the effect of differing nitric acid contents of the 1,10-decanedicarboxylic acid on the color qualities of the distillate and on the residue formation during distillation. In the prior art processes, color numbers of about 700 APHA are generally attained.

| Percent of Free HNO₃ in the Crude DDA | Dist. Temp. Sump ° C. | Head ° C. | Pressure in Torr. | Distillate Melt Color Number APHA | Residue |
|---|---|---|---|---|---|
| 0.1 | 230 | 200 | 1-2.5 | >1,000 | 23% strong decomp. |
| 0.05 | 228-230 | 200 | 1.2 | 700 | 10-15% |
| 0.03 | 225 | 198 | 0.9-1 | 400 | 8% |
| 0.02 | 220 | 195 | 0.9 | 150 | 4-6% |
| 0.01 | 218 | 190 | 0.6 | 90-100 | 2% |
| 0.01 | 218 | 190 | 0.6 | 50 | 1% |

Above 0.02% by weight of nitric acid content, distillates are obtained having an unsatisfactory color quality (The American Public Health Association APHA color numbers given in the tables herein represent the color of the melt measured at 150° C. under deoxo nitrogen [ASTM-D 1209]).

Free nitric acid content is determined by acid number (ASTM-D 664 modified). At higher nitric acid contents, residues are formed to an increasing extent which impair the economics of the process. Preferably, the free nitric acid content of the 1,10-decanedicarboxylic acid which is distilled is about 0.01% by weight or even lower. However, contents substantially below 0.01% by weight can be achieved only at great expense and thus adversely affect the economics of the process.

To adjust the nitric acid content to 0.01% by weight or less, the crude acid can be heated, preferably at a pressure of 2-500 torr. and at a temperature of 150°-200° C. until the evolution of nitrous gases has substantially terminated. This process is normally conducted by heating the crude acid to 150° C. and gradually lowering the pressure. At about 500 torr., the evolution of nitrous gases commences. Thereafter, the pressure is gradually lowered further and simultaneously the temperature is slowly raised until at about 200° C. and about 2 torr., the formation of nitrous gases ceases.

Normally, since the water content of crude 1,10-decanedicarboxylic acid is substantially greater than 0.1% by weight, the water content thereof is also lowered in the process of this invention to 0.1% by weight or less. If a thermal treatment of the crude decanedicarboxylic acid to remove excess nitric acid is employed, the water content is also reduced during this treatment to 0.1% by weight or less.

It is advantageous, when conducting this method of reducing the free nitric acid content of the 1,10-decanedicarboxylic acid to 0.02% by weight or less prior to distillation, to remove the mother liquor from the nitric acid oxidation reaction mixture, for example, by filtration, centrifuging, or vacuum-filtering, and then displace any mother liquor still adhering to the crude acid by an essentially one-time water treatment.

In general, it is preferable to lower the content of free nitric acid to the value of this invention by washing out with water; in this process, the introduction of additional water into the starting material must be tolerated. However, such excess water can readily be removed in the process of this invention.

According to the invention, the water content of 1,10-decanedicarboxylic acid, determined according to Fischer (ASTM-D 1744), prior to distillation, must be 0.1% by weight or below, preferably 0.05 - 0.1% by weight or below. At above 0.1% by weight, the vacuum required for the distillation step of this invention cannot be achieved or the time required to achieve it is excessive, so that the acid is heated to a temperature which is too high or for a period of time which is too long during the distillation, with resulting loss of quality, e.g., color value.

In order to remove the excess water, it is generally sufficient to heat the starting compound, prior to distillation, to 150°-180° C. under a partial pressure of 760-500 torr. The duration of the dewatering step depends on the water content of the starting 1,10-decanedicarboxylic acid. To achieve water contents substantially below 0.1% by weight generally involves excessive costs. If a water content of no more than about 0.3% by weight is achieved, it is also possible to lower the water content to about 0.1% by weight, specifically in a continuous mode of operation, by removing the water in a preliminary distillation column, together with a minor amount of forerun. The sump of this preliminary column is then distilled in accordance with the process of this invention.

Once the organically bound nitrogen, free nitric acid, and/or water contents of the 1,10-decanedicarboxylic acid have been reduced to the maximum permissible values by appropriate treatment of the crude acid, the 1,10-decanedicarboxylic acid is then distilled. In the distillation, reflux must be substantially completely avoided. For this purpose, it is advantageous to heat the portion of the column through which the volatilized acid passes.

To keep the thermal load on the 1,10-decanedicarboxylic acid at a low value during the distillation, the latter is conducted at a sump temperature of 215°-225° C. Above 225° C., thermal decomposition reactions can occur; below 215° C., the product does not volatilize rapidly enough.

The distillation is conducted at a pressure of 2 - 0.5 torr. Above 2 torr., the product must be heated too highly in order for it to boil, whereas pressures of below 0.5 torr., though being advantageous, can be reached only at greater technical expenditures. During the distillation, the pressure difference in the distillation apparatus, e.g., between the sump and the heat of the column, should be maintained at a minimum value, since otherwise the product is heated up too much during the distillation, for example, in the sump. Advantageously, an empty tube and/or a column filled at most to the halfway mark with Raschig rings are utilized as the distillation column.

To conduct the distillation of the 1,10-decanedicarboxylic acid under maximum gentle conditions, it is advantageous to effect a thin-film evaporation, so that the residence times on the evaporator surfaces are shortened. It is also advantageous to evaporate the product from as large a surface area as possibble. For this purpose, thin-film evaporator apparatus conventional in the art can be employed.

Advantageously, forced-circulation evaporators or rapid-throughflow evaporators are utilized which are preferably falling-film evaporators. In this type of evaporator, suitable devices, e.g., nozzles, are provided above the individual boiling tubes, making it possible to allow the product to flow downwardly in the interior of the evaporator tubes in the form of a maximally uniform and optionally rotating film. The amount of the charge is adjusted so that the entire heat exchange surface remains wetted with a liquid film.

The process of this invention can be conducted continuously as well as batch-wise.

The 1,10-decanedicarboxylic acid obtained according to the process of the present invention generally has a purity of 98-99.5% by weight and color numbers of 50-80 APHA. Due to its high purity, this acid is eminently suitable as a building block for the production of polyamides and polyesters. Due to its good color qualities, the acid can be utilized very advantageously as a fiber component.

The process of this invention surprisingly makes it possible to economically obtain high quality 1,10-decanedicarboxylic acid with very good color number by a simple method involving low working-up losses.

The drawing is a flow sheet showing the prior art steps for producing the starting crude crystalline 1,10-decanedicarboxylic acid and those employed in the novel process for producing polymer quality product.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

One-Stage Distillation

Starting Product

The crude 1,10-decanedicarboxylic acid produced in accordance with U.S. Pat. No. 3,761,517 at an oxidation temperature of 40° C. is separated from the discharged reaction mixture by centrifuging. The thus-separated, crystalline 1,10-decanedicarboxylic acid is washed on the centrifuge with water to remove the adhering nitric acid and is thereafter dried in a hurdle drying chamber at 100°–110° C. and under a pressure of 100 torr. After drying, the water content of the acid is 0.1% by weight. The thus-obtained crude, 1,10-decanedicarboxylic acid has the following characteristic data:

| | | |
|---|---|---|
| Solidifying point | 127.4 | ° C. |
| Melt color number (150° C., at once) | 400 | APHA |
| Melt color number (150° C., after 2 hours) | 900 | APHA |
| N content (organically bound) | 0.016 | % by wt. |
| Free HNO$_3$ | 0.01 | % by wt. |
| Ash | 200 | mg./kg. |
| Heavy metals | 25 | mg./kg. |
| Analytical Composition: | | |
| Decanedicarboxylic acid | 98.5 | % by Wt. |
| Nonanedicarboxylic acid | 1.0 | % by Wt. |
| Sebacic acid | 0.18 | % by Wt. |
| Azelaic acid | 0.04 | % by Wt. |
| Low-boiling components | 0.28 | % by Wt. |

Distillation Apparatus

Column without packing, h = 6 m., d = 0.35 m., sump = 2.3 m$^3$ capacity. The required heat is supplied to the system by way of a falling-film evaporator (3 m$^2$). The heating medium is a thermal oil evaporated in a suitable heating unit. The sump and the column are heated with high-pressure steam. The column is equipped with a vacuum system (steam jet unit), by means of which a pressure of 0.5 torr can be reached at the head of the column. A crystal-precipitating system is mounted between the column and the steam jet unit.

The dry, crude decanedicarboxylic acid (water content 0.1% by weight) is melted in a crucible (selectively, it is also possible to melt water-moist decanedicarboxylic acid, carrying out the dewatering step simultaneously, see Example 2) and is continuously fed to a falling-film evaporator. The content of the sump is continuously circulated over the falling-film evaporator by means of a circulating pump. The distillation receiver is charged with deoxo-N$_2$.

| Distillation Conditions | | |
|---|---|---|
| Temperatures: | | |
| Crucible | 155 | ° C. |
| Sump | 215 | ° C. |
| Column - center | 210 | ° C. |
| Column - head | 190 | ° C. |
| Pressures: | | |
| Column - head | 0.5 | torr |
| p | 25–35 | mm. H$_2$O column |
| Feed: | 153 | kg./h. |
| Residue: | 1.5–2 | % based on the feed |
| Distillate: | 150 | kg./h. |
| Solidifying point | 128.0 | ° C. |
| Melt color number (150° C., immediately | 50 | APHA |
| Melt color number (150° C., after 2 hours) | 70 | APHA |
| N content (organically bound) | 0.005 | % by Wt. |
| Free HNO$_3$ | not | detectable |
| Ash | 10 | mg./kg. |
| Heavy metals | not | detectable |
| Analytical Composition: | | |
| 1,10-Decanedicarboxylic acid | 98.74 | % by Wt. |
| Nonanedicarboxylic acid | 0.97 | % by Wt. |
| Sebacic acid | 0.15 | % by Wt. |
| Azelaic acid | 0.03 | % by Wt. |
| Low acids | 0.11 | % by Wt. |

The decanedicarboxylic acid of the above quality, purified by distillation, is suitable for the manufacture of polyamides and polyesters, as determined by commercial use.

EXAMPLE 2

Two-Stage Continuous Distillation

Starting Product

The same crude acid is employed as described in Example 1 (see the above for analytical composition). In contrast to Example 1, the acid is not dried previously.

Distillation Apparatus

Two-liter melt agitator vessel, electrically heated, with a descending cooler.

| | |
|---|---|
| Forerun column: | h = 500 mm., d = 30 mm., electric attendant heater, filled to the halfway mark with Raschig rings |

-continued

| | |
|---|---|
| Alembic: | 2 liters, heated electrically |
| Main run column: | h = 500 mm., d = 30 mm., electric heater |
| Alembic: | 2 liters, heated electrically |
| Vaccum unit: | rotary-slide oil pump |

Crucible

The moist, crude decanedicarboxylic acid, having a water content of 25% by weight, is melted at a temperature of 150°-160° C., the water being removed during this step within 60 minutes at 760 torr by way of a descending cooler. The melt continuously withdrawn from the bottom of this vessel and being introduced into the sump of the following (forerun) column has a residual moisture of 0.20 - 0.30% by weight.

| | | | |
|---|---|---|---|
| Forerun Column: | | | |
| Temperature: | Head | 205-215 | ° C. |
| | Sump | 220-230 | ° C. |
| Head Pressure: | | 0.7-1.0 | torr |
| Reflux ratio | | 1 : 3 | |
| Feed | | 1 | kg./h. (anhydrous melt) |
| Forerun: | | 50 | g./h. |
| Analytical Composition/Forerun: | | | |
| Decanedicarboxylic acid | | 88.20 | % by Wt. |
| Nonanedicarboxylic acid | | 4.90 | % by Wt. |
| Sebacic acid | | 1.11 | % by Wt. |
| Azelaic acid | | 0.33 | % by Wt. |
| Low-boiling components | | 5.46 | % by Wt. |

The sump of this forerun column, water content = 0.05% by weight, is continuously introduced into the main run column.

| | | | |
|---|---|---|---|
| Main Run Column | | | |
| Temperature: | Head | 192 | ° C. |
| | Sump | 217 | ° C. |
| Head Pressure: | | 0.5 | torr |
| Distillate: | | 930 | g./h. |
| Solidifying point | | 128.5 | ° C. |
| Melt color number (150° C., immediately) | | 40 | APHA |
| Melt color number (150° C., after 2 hours) | | 60 | APHA |
| N content (organically bound) | | 0.003 | % by Wt. |
| Free HNO₃ | | not | detectable |
| Ash | | < 5 | mg./kg. |
| Heavy metals | | not | detectable |
| Analytical Composition: | | | |
| Decanedicarboxylic acid | | 99.62 | % by Wt. |
| Nonanedicarboxylic acid | | 0.26 | % by Wt. |
| Sebacic acid | | 0.06 | % by Wt. |
| Azelaic acid | | 0.01 | % by Wt. |
| Low-boiling components | | 0.05 | % by Wt. |
| Residue: | | 20 | g./h. |

If, in place thereof, a crude DDA is used having a free HNO₃ content of > 0.1% by weight, a decomposition is observed in all cases under the distillation conditions (empty tube and/or packed column), with the consequence that strong vacuum fluctuations occur and high sump and head temperatures must be maintained to sustain the distillation. The distillate is discolored ( > 500 - 1,000 APHA). The amount of residue is 15-20% by weight, based on the starting material.

EXAMPLE 3

The oxidation of cyclododecanol with nitric acid in the presence of an ammonium vanadate catalyst is conducted at 35° C. The content of organically bound nitrogen in the crude decanedicarboxylic acid is approximately 1,000 p.p.m. The oxidation product is subjected directly to a thermal aftertreatment at 85° C., thus reducing the content of organically bound nitrogen in the crude decanedicarboxylic acid to practically 100 p.p.m.

The contents of free nitric acid and water are lowered as described in Example 1.

The starting compound has the following characteristic data:

| | | |
|---|---|---|
| Solidifying point | 127.5 | ° C. |
| Melt color number (150° C., immediately) | 350 | APHA |
| Melt color number (150° C., after 2 hours) | 800 | APHA |
| N content (organically bound) | 0.010 | % by Wt. |
| Free HNO₃ | 0.009 | % by Wt. |
| Ash | 170 | mg./kg. |
| Heavy metals | 21 | mg./kg. |
| Analytical Composition: | | |
| Decanedicarboxylic acid | 98.8 | % by Wt. |
| Nonanedicarboxylic acid | 0.8 | % by Wt. |
| Sebacic acid | 0.16 | % by Wt. |
| Azelaic acid | 0.03 | % by Wt. |
| Low-boiling components | 0.21 | % by Wt. |

The distillation is conducted as set forth in Example 1.

| | | |
|---|---|---|
| Distillate: | | |
| Solidifying point | 128.2 | ° C. |
| Melt color number (150° C., immediately) | 50 | APHA |
| Melt color number (150° C., after 2 hours) | 70 | APHA |
| N content (organically bound) | 0.004 | % by Wt. |
| Free HNO₃ | not | detectable |
| Ash | <10 | mg./kg. |
| Heavy metals | not | detectable |
| Analytical Composition: | | |
| Decanedicarboxylic acid | 98.95 | % by Wt. |
| Nonanedicarboxylic acid | 0.70 | % by Wt. |
| Sebacic acid | 0.14 | % by Wt. |
| Azelaic acid | 0.03 | % by Wt. |
| Low-boiling components | 0.18 | % by Wt. |

EXAMPLE 4

The oxidation of cyclododecanol/one with nitric acid in the presence of a vanadium catalyst is conducted at a temperature of 50° C. The content of organic nitrogen compounds in the thus-obtained di-acid amounts to 1,200 p.p.m. Subsequently to the immediately following aftertreatment of the oxidation product at 85° C., the content of organically bound nitrogen has dropped to about 300 p.p.m.

The crystalline crude decanedicarboxylic acid is separated from the crystal slurry by filtration. The mother liquor adhering to the crystals is removed by a one-time treatment with water. The crude acid then contains 0.035% by weight of free nitric acid. Thereafter, the crude acid is heated to 150°-180° C. while gradually lowering the pressure. At about 500 torr, nitrous gases are being formed. After the gas evolution has faded, the temperature is maintained at 180° C. and the pressure lowered to 2 torr. After this treatment, the free nitric acid content is < 0.001% by weight; the water content is < 0.1% by weight.

The subsequent distillation is conducted as indicated in Example 1. The analytical data of the thus-obtained 1,10-decanedicarboxylic acid coincide essentially with those set forth in Example 1. The residue, based on the feed, is in this case 2.5% by weight. The APHA color number has a value of 70 immediately after the distillation, measured at 150° C. under deoxo nitrogen (ASTM-D 1209).

The peceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of 1,10-decanedicarboxylic acid with low melt color values from crude crystalline acid having an organically bound nitrogen content of 0.05% by weight or less and having a nitric acid content above 0.1% by weight and produced by oxidizing cyclododecanol, cyclododecanone or both with nitric acid at low temperature and under mild conditions and subjecting the thus-produced crude acid to a thermal treatment under oxidative conditions, at a temperature above the oxidation temperature, which reduces the organically bound nitrogen content of the crude acid to 0.05% by weight or less, which consists essentially of (a) reducing the nitric acid content of the starting crystalline crude acid to 0.02% by weight or less by a thermal treatment of the crude acid under vacuum at a temperature at which nitrous gases evolve from the crude acid and above the oxidation and thermal treatment temperatures employed to produce the starting crude crystalline acid; (b) distilling the thus pre-purified 1,10-decanedicarboxylic acid at a sump temperature of 215°–225° C. and at a pressure of 0.5 – 2 torr.; and (c) recovering the 1,10-decanedicarboxylic acid as the distillate.

2. A process according to claim 1, wherein the thermal treatment step (a) is conducted at 150°–180° C. and at a pressure of 500–760 torr.

3. A process according to claim 1, wherein in the distillation step the 1,10-decanedicarboxylic acid is evaporated by thin-film evaporation.

4. A process according to claim 1, wherein the 1,10-decanedicarboxylic acid is evaporated during distillation in a falling-film evaporator.

5. A process for the production of 1,10-decanedicarboxylic acid with low melt color values from crude crystalline acid having an organically bound nitrogen content of 0.05% by weight or less and having a nitric acid content above 0.1% by weight and produced by oxidizing cyclododecanol, cyclododecanone or both with nitric acid at low temperature and under mild conditions and subjecting the thus-obtained crude acid to a thermal treatment under oxidative conditions, at a temperature above the oxidation temperature, which reduces the organically bound nitrogen content of the crude acid to 0.05% by weight or less, which consists essentially of (a) reducing the nitric acid content of the starting crystalline crude acid to 0.02% by weight or less by washing the crude acid with water and drying the washed acid to a water content of 0.1% by weight or less; (b) distilling the thus pre-purified 1,10-decanedicarboxylic acid at a sump temperature of 215°–225° C. and at a pressure of 0.5–2 torr.; and (c) recovering the 1,10-decanedicarboxylic acid as the distillate.

6. A process according to claim 5, wherein in the distillation step the 1,10-decanedicarboxylic acid is evaporated by thin-film evaporation.

7. A process according to claim 5, wherein the 1,10-decanedicarboxylic acid is evaporated during distillation in a falling-film evaporator.

8. A process for the production of 1,10-decanedicarboxylic acid with low melt color values from crude crystalline acid having an organically bound nitrogen content of 0.05% by weight or less and having a nitric acid content above 0.1% by weight and produced by oxidizing cyclododecanol, cyclododecanone or both with nitric acid at low temperature and under mild conditions and subjecting the thus-produced crude acid to a thermal treatment under oxidative conditions, at a temperature above the oxidation temperature, which reduces the organically bound nitrogen content of the crude acid to 0.05% by weight or less, which consists essentially of (a) reducing the nitric acid content of the starting crystalline crude acid to 0.2% by weight or less by washing the crude acid with water and subjecting the washed acid to a thermal treatment under vacuum at a temperature at which nitrous gases evolve from the crude acid and above the oxidation and thermal treatment temperatures employed to produce the starting crude crystalline acid; (b) distilling the thus pre-purified 1,10-decanedicarboxylic acid at a sump temperature of 215°–225° C. and at a pressure of 0.5–2 torr.; and (c) recovering the 1,10-decanedicarboxylic acid as the distillate.

9. A process according to claim 8, wherein the thermal treatment step is conducted at 150°–180° C. and at a pressure of 500–760 torr.

10. A process according to claim 8, wherein in the distillation step the 1,10-decanedicarboxylic acid is evaporated by thin-film evaporation.

11. A process according to claim 8, wherein the 1,10-decanedicarboxylic acid is evaporated during distillation in a falling-film evaporator.

12. A process according to claim 8, wherein the washed acid is dried prior to the thermal treatment step.

* * * * *

UNITED STATES PATENT AND TRADEMARK OFFICE
CERTIFICATE OF CORRECTION

PATENT NO. : 4,067,779
DATED : January 10, 1978
INVENTOR(S) : FERDINAND LIST ET AL.

It is certified that error appears in the above-identified patent and that said Letters Patent are hereby corrected as shown below:

The Assignee should read -- CHEMISCHE WERKE HUELS AKTIENGESELLSCHAFT, Marl, Germany --.

Signed and Sealed this

Eighteenth Day of April 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,067,779
DATED : January 10, 1978
INVENTOR(S) : Ferdinand List et al.

It is certified that error appears in the above-identified patent and that said Letters Patent is hereby corrected as shown below:

Column 10, line 32:

reads "starting crystalline crude acid to 0.2% by weight or less"

Signed and Sealed this

Twenty-second Day of February 1983

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,067,779
DATED : January 10, 1978
INVENTOR(S) : FERDINAND LIST ET AL It is certified that error appears in the above-identified patent and that said Letters Patent is hereby corrected as shown below:

Column 10, line 32:

reads "starting crystalline crude acid to 0.2% by weight or less"

should read -- starting crystalline crude acid to 0.02% by weight or less -- .

This certificate supersedes Certificate of Correction issued February 22, 1983.

Signed and Sealed this

Thirty-first Day of July 1984

[SEAL]

Attest:

Attesting Officer

GERALD J. MOSSINGHOFF

Commissioner of Patents and Trademarks